United States Patent [19]

Catlin

[11] Patent Number: 5,195,980

[45] Date of Patent: Mar. 23, 1993

[54] HEMOSTATIC VALVE

[75] Inventor: David G. Catlin, West Chester, Pa.

[73] Assignee: Thomas Medical Products, Inc., Malvern, Pa.

[21] Appl. No.: 816,988

[22] Filed: Jan. 3, 1992

[51] Int. Cl.$^5$ ............................................. A61M 5/00
[52] U.S. Cl. ................................... 604/167; 604/256
[58] Field of Search ............................. 604/167, 256

[56] References Cited

U.S. PATENT DOCUMENTS

| | | | |
|---|---|---|---|
| 4,341,239 | 7/1982 | Atkinson . | |
| 4,421,296 | 12/1983 | Stephens | 604/256 |
| 4,581,020 | 4/1986 | Mittleman | 604/256 |
| 4,610,469 | 9/1986 | Wolff-Mooij | 251/149.7 |
| 4,634,432 | 1/1987 | Kocak | 604/167 |
| 4,636,668 | 1/1987 | Leverberg et al. | 251/149.7 |
| 4,935,010 | 6/1990 | Cox et al. | 604/167 |
| 4,960,412 | 10/1990 | Fink | 604/167 |
| 5,057,084 | 10/1991 | Ensminger et al. | 604/167 |
| 5,085,645 | 2/1992 | Purdy et al. | 604/256 |
| 5,092,840 | 3/1992 | Healy | 604/167 |
| 5,106,054 | 4/1992 | Mollenauer | 604/167 |

Primary Examiner—Paul J. Hirsch
Attorney, Agent, or Firm—Caesar, Rivise, Bernstein, Cohen & Pokotilow, Ltd.

[57] ABSTRACT

A Y-connector including a hemostatic valve for enabling the introduction of an elongated member, e.g., a balloon catheter, into the body of a living being while precluding blood from flowing out of the valve. The Y-connector includes a housing having an interior in which a pair of resilient valve elements and a plunger mechanism are located. One valve element, e.g., a disk-like member, has a small diameter opening therein. The other valve element, e.g., a duck-bill valve elements, includes a normally closed, but openable, aperture therein. The plunger mechanism includes a tubular member having an outer diameter which is smaller than the diameter of the opening in the one valve element. The tubular member is arranged to be moved into and out of the opening in the one valve member and into and out of the aperture in the other valve element. The tubular member has a central passageway arranged to enable the elongated member to be readily extended therethrough for location at a desired position within the body of the being. The one valve element is arranged for engaging the periphery of the elongated member after the elongated member has been extended through the passageway and after the tubular member is moved out of the opening in the valve member to preclude blood from flowing through the interface between the valve member and the elongated member.

10 Claims, 2 Drawing Sheets

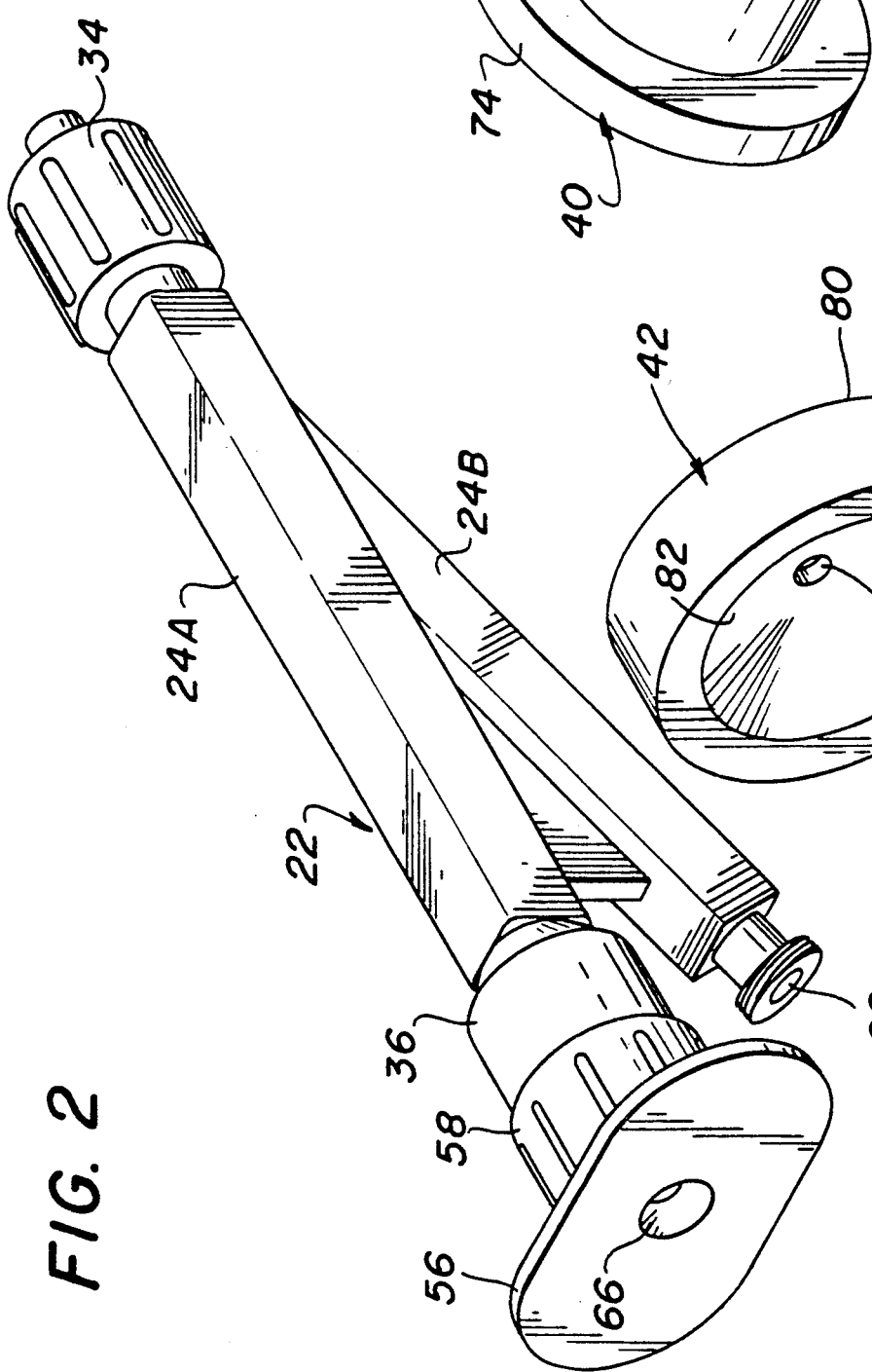

ســ5,195,980

HEMOSTATIC VALVE

BACKGROUND OF THE INVENTION

This invention relates generally to medical devices and more particularly to hemostatic valves.

When access to the vascular system is required, control of bleeding is essential. Thus various connectors or other devices used for intravascular applications make use of a hemostatic valve to enable a catheter or other small diameter instrument to be introduced into the body of a living being while precluding blood from flowing out of the connector. For example, in angioplasty it is a common practice to introduce an angioplasty catheter, e.g., a balloon catheter, through a hemostatic valve located within a connector. The hemostatic valve and its associated connector is used with a conventional guiding catheter to guide a tubular portion of the connector into the interior of the patient's artery. The hemostatic valve ensures that blood does not flow out of the connector, while enabling the angioplasty catheter to be passed therethrough One common type of hemostatic valve is the so called "Tuohy Borst" valve. That valve comprises an elastomeric, e.g., silicone, membrane having an opening through which the catheter extends and which is closed about the periphery of the catheter by the rotation of a cap to establish hemostasis.

While such a valve is generally suitable for its intended purpose, it nevertheless leaves much to be desired from the standpoints of functionality and ease of use. In this regard connectors employing a "Tuohy Borst" valve require the use of a separate introducer needle or tube to pass through the valve to open its membrane so that the balloon catheter can be safely passed therethrough without damage (conventional balloon angioplasty catheters and angioplasty guidewires are quite delicate and are susceptible to damage if they are attempted to be pushed directly through a Tuohy Borst valve membrane). Thus, after the separate introducer needle or tube is in place in the Tuohy Borst valve a conventional guidewire is passed through the needle or tube. The introducer needle or tube is then removed, the balloon catheter inserted, and the connector's cap tightened to bring its valve membrane tightly into engagement about the periphery of the balloon catheter to effect hemostasis.

During the placement of the introducer needle through the valve, and until the valve is closed about the periphery of the balloon catheter, blood may flow out through the valve. Moreover, since the valve membrane is brought into tight peripheral engagement with the balloon catheter, maneuverability of the catheter by the physician is compromised, if not precluded, e.g., it is difficult if not impossible to move the catheter either longitudinally or rotationally with respect to the hemostatic valve.

OBJECTS OF THE INVENTION

Accordingly, it is a general object of this invention to provide a hemostatic valve which overcomes disadvantages of the prior art.

It is further object of this invention to provide a hemostatic valve which enables an elongated device, e.g., a catheter, guidewire, stent, or other medical device, to be readily extended therethrough while precluding blood from flowing out of the valve.

It is still a further object of this invention to provide a hemostatic valve which enables an elongated device to be readily extended therethrough without requiring the use of any separate introducer.

It is still a further object of this invention to provide a hemostatic valve in a device which is capable of one-handed operation.

It is yet a further objects of this invention to provide a hemostatic valve which effects a hemostatic seal with an elongated member, such as a catheter, extending therethrough, while enabling the member to be readily moved longitudinally and rotationally within the valve.

It is yet a further object of this invention to provide a hemostatic valve which is simple in construction.

SUMMARY OF THE INVENTION

These and other objects of this invention are achieved by providing a hemostatic valve for use in a device enabling the introduction of an elongated member, e.g., a balloon catheter, into the body of a living being while precluding blood from flowing out of the valve. The device includes a housing. The hemostatic valve comprises valve means and plunger means. The housing has a hollow interior portion in which the valve means is located.

The valve means comprises at least one resilient valve member having a small diameter opening therein. The plunger means comprises a tubular member having an outer diameter which is larger than the diameter of the opening. The tubular member is arranged to be moved into and out of the opening in the valve member and has a central passageway arranged to enable the elongated member to be readily extended therethrough for location at a desired position within the body of the being.

The valve member is arranged for engaging the periphery of the elongated member after the elongated member has been extended through the passageway and after the tubular member is moved out of the opening in the valve member to preclude blood from flowing through the interface between the valve member and the elongated member.

DESCRIPTION OF THE DRAWINGS

Other objects and many attendant features of this invention will become readily appreciated as the same becomes better understood by reference to the following detailed description when considered in connection with the accompanying drawings wherein:

FIG. 2 is a reduced, isometric view of the Y-connector shown in FIG. 1;

FIG. 3 is an enlarged, isometric view of one of the valve elements making up the hemostatic valve shown in FIG. 1; and FIG. 4 is an enlarged, isometric view of another of the valve elements making up the hemostatic valve shown in FIG. 1.

DETAILED DESCRIPTION OF THE PREFERRED EMBODIMENTS

Figure 1:
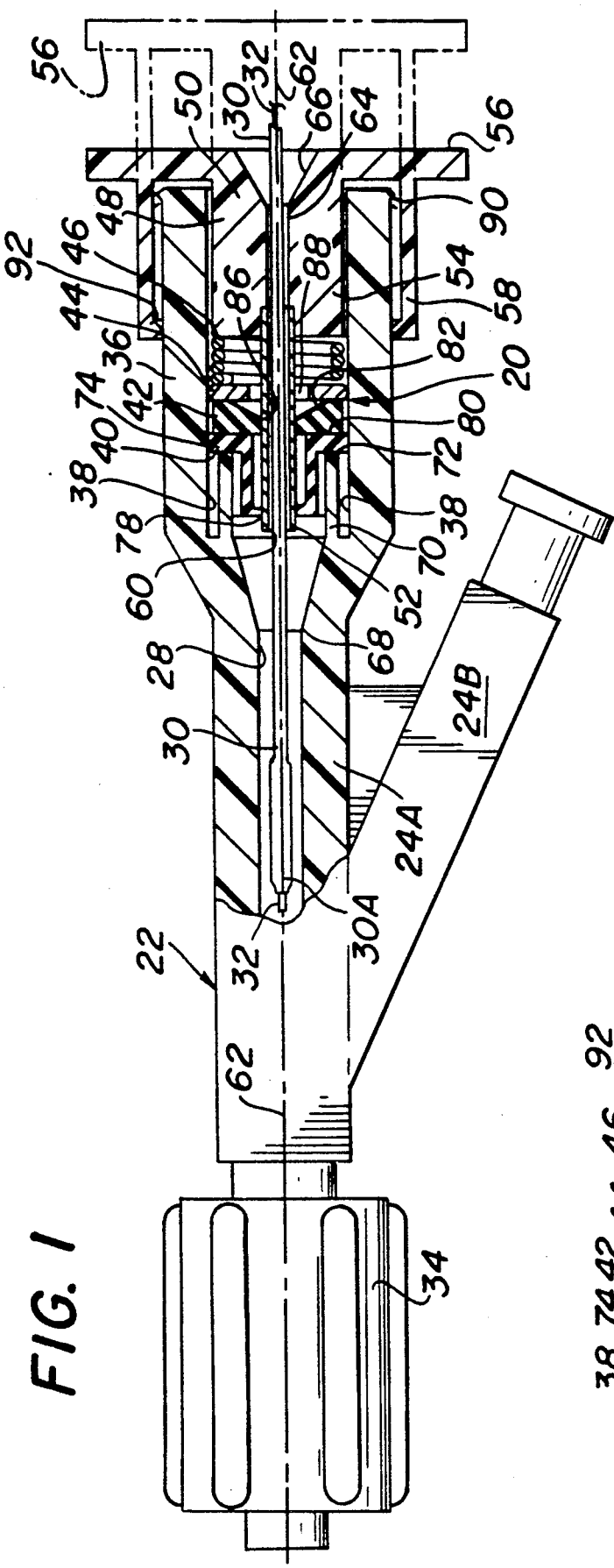
FIG. 1 is a plan view, partially in section, showing a Y-connector utilizing a hemostatic valve constructed in accordance with this invention shown during the procedure of introducing a conventional guidewire and angioplasty catheter therethrough.

Referring now to the various FIGURES of the drawing wherein like reference characters refer to like parts, there is shown at 20 in FIG. 1, a hemostatic valve assembly constructed in accordance with this invention and housed within a connector 22. The connector 22 is a "Y-connector" which is a conventional type of device including an elongated main section 24A and a angularly extending section 24B. These two sections are formed, e.g., molded, as an integral unit of any suitable material, e.g., plastic.

As is conventional, the main section 24 of the connector 22 includes a central passageway 28 extending longitudinally through the entire length of the main section. It is through this central passageway 28 that a catheter 30 and any other instrument or device, e.g., a conventional guidewire 32, is passed. The distal end of the connector 22 includes a conventional rotatable luer adapter 34 arranged to be secured to a corresponding member (not shown) at the proximal end of a guide catheter (not shown).

The guide catheter is arranged to extend into the body of the patient. In particular, for angioplasty applications the guide catheter is extended percutaneously into an artery, e.g., the femoral artery, of the patient so that a guidewire 32 and a catheter 30 having a balloon 30A at its distal end can be inserted into the patient's femoral artery and from there advanced through the vascular system to a desired position.

As shown clearly in FIG. 2 the proximal end of the connector 22 is in the form of an enlarged housing portion 36 of circular cylindrical shape defining a hollow interior chamber 38 (FIG. 1) therein. This chamber is in communication with the central passageway 28 and is open to the end of the housing portion 36. The hemostatic valve assembly 20 of this invention is located within the chamber 38.

As will be described in detail later the hemostatic valve assembly 20 is operable to enable the guide wire 32 and the balloon catheter 30 (or any other small diameter elongated member) to be readily passed through it into the communicating passageway 28, through the connected guide catheter into the patient's artery. Once the catheter and/or guidewire is (are) extended therethrough portions of the valve assembly 20 (to be described later) hemostatically engage the catheter and/or guidewire to thereby seal the connector so that blood cannot flow out of the connector, while still enabling the physician to manipulate the catheter or guidewire with respect to the connector.

The angularly extending section 24B of the connector 22 includes a longitudinally extending passageway 26 (FIG. 2) which merges with the passageway 28 in the main section and serves as a means for introducing some material, e.g., a contrast or imaging medium, into the connector to flow into the main passageway 28 and from there through the connected introducer catheter into the patient's artery.

Before discussing the details of hemostatic valve constructed in accordance with the teachings of this invention it should be pointed out that such a valve can be used in other types of connectors or structures through which a catheter or other flexible tube or elongated instrument is to be passed so that access can be had to the interior of a living being's body, while precluding the egress of blood therefrom. The inclusion of the hemostatic valve assembly 20 in a Y-connector 22 is, thus, merely exemplary. For example, the hemostatic valve of this invention may be configured as a stand-alone unit.

Figure 1A:
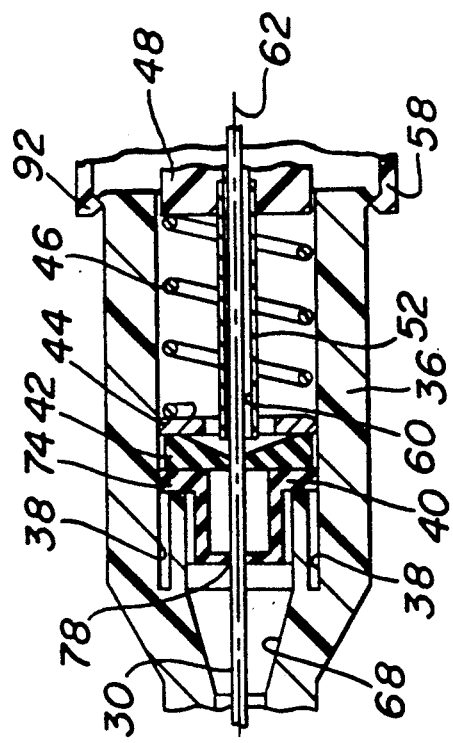
FIG. 1A is a plan view of a portion of the hemostatic Y-connector of FIG. 1 and showing the hemostatic valve in operation to seal the Y-connector after the conventional guidewire and angioplasty catheter has been inserted therethrough.

Turning now to FIGS. 1, 1A, 3 and 4 the details of the hemostatic valve assembly 20 will now be described. As can be seen therein that assembly basically comprises a first valve element 40 (FIG. 3), a second valve element 42 (FIG. 4), a retaining member 44 (FIGS. 1 and 1A), a biasing spring 46 (FIGS. 1 and 1A), and a plunger subassembly 48 (FIGS. 1 and 1A). The plunger subassembly basically comprises a plunger 50 and a cylindrical access tube or needle 52.

The plunger is formed as an integral unit, e.g., molded of plastic, and basically comprises a cylindrical central core 54, a flat cap 56, and an annular flange 58. The central core 54 of the plunger is disposed within the chamber 38. The annular flange 58 is spaced from the central core 54 so that when the central core is located within the chamber 38 the flange 58 surrounds the outer periphery at the free end of housing portion 6. As can be seen in FIG. 2, the cap 56 is a flat-oval shaped member which projects outward from the flange 58.

The access tube 52 is an elongated, linear tube formed of any suitable material, e.g., a plastic or metal, and has a central passageway 60 extending therethrough. The tube 52 projects inward along the central longitudinal axis 62 of the connector section 24 from the inner end of the plunger's central core 54. The internal diameter of the passageway 60 is sufficiently large to enable a conventional balloon catheter 30 to be extended therethrough.

The plunger 50 includes a central bore 64 extending through it coaxially with the central longitudinal axis 62. The entrance to the bore at the top of the cap 56 is in the form of a flared mouth 66 to facilitate the introduction of the guidewire 2 and catheter 30 therein. The proximal end of the access tube 2 is located within an annular ledge at the distal end of the bore 64 and is secured in place by any suitable means, e.g., an adhesive, a weldment, etc., so that the bore 64 in the plunger and the passageway 60 of the access tube are axially aligned and in communication with each other.

The distal end of the cavity 38 includes a tapered wall 68 merging into the proximal end of the central passageway 28. An annular flange 70 extends about the periphery of the tapered wall 68 and includes a top surface or seat 72 on which the first valve element 40 is seated.

Referring to FIGS. 1 and 3 it can be seen that the valve element 40 is a conventional "duck-bill" type, check valve, such as that disclosed in U.S. Letters Pat. No. 4,341,239. That valve is formed as an integral member of a resilient material, e.g., latex, and includes a peripheral flange 74 which is the portion of the valve element which is disposed on the seat 72. The central portion of the valve element 40 is cup shaped and includes a pair of diametrically oriented ribs 76 and a transversely extending slit 78. The slit 78 extends perpendicularly to the plane of the ribs 76 and is normally closed but is arranged to be opened by the access tube 52 being extended therethrough (as will be described later).

The other valve element 42 is disposed immediately adjacent the valve element 40. The valve element 42 is not a conventional member, but rather is constructed in accordance with one aspect of this invention. The element 42 is best seen in FIGS. 1, 1A, and 4 and basically comprises a circular, disk-like member formed of a resilient material, e.g., silicone, having a planar distal face 80 and a concave proximal face made up of a conical surface 82 located centrally within a circular, planar surface 84.

A central opening 86 extends through the valve element 42 at the nadir of the conical surface 82. The opening 86 is circular and has an inner diameter which is less than the outer diameter of the guidewire 32, balloon catheter 30, or any other instrument or device which is arranged to be passed through the hemostatic valve 20.

The retaining member 44 basically comprises a flat, disk-like member, e.g., a washer, having a relatively large hole 88 at its center. The retaining member is located within the chamber 38 so that its distal surface abuts the proximal planar surface 84 of the valve element 42. The valve element 42 is located so that its distal planar surface 80 abuts the planar proximal surface of the flange 74 of the duck-bill valve element 40.

The spring 46 basically comprises a helical, compression spring formed of any suitable material, e.g., plastic or metal, and which is interposed between the proximal face of the retaining washer 44 and the inner face of the plunger core 54. With the spring 46 so located it tends to naturally bias or push the plunger subassembly 50 in the proximal direction to a retracted position shown by the phantom lines in FIG. 1 and by the solid lines in FIG. 1A. When the plunger subassembly is in the retracted position the free (distal) end of the access tube 52 is located proximally of the valve elements 40 and 42. At this time if no instrument or device is extended through the hemostatic valve 20 the slit 78 in the valve element 42 will be closed to preclude blood from flowing from the artery out through the connector 22.

The plunger subassembly 48 is arranged to be moved against the bias of the spring 46 to the full line position shown in FIG. 1 by the application of manual pressure to the head of the plunger. Such action can be readily accomplished by the user holding the connector 22 in one hand while using the thumb of that hand to press the plunger 50 into the interior of the chamber 38. The movement of the plunger subassembly in the distal direction cause the free end of the access tube 52 to first enter into and through the opening 84 in the valve element 42 by stretching the material making up that element. Continued movement of the subassembly in the distal direction causes the free end of the access tube 52 to enter into and through the slit 78 in the duck bill valve element 40, thereby opening it. Accordingly, a clear or free path is provided through the valve elements 40 and 42 by the access tube 52 so long as the access tube extends through those elements, i.e., so long as the physician maintains pressure on the plunger cap 56.

The guidewire 32 and the balloon catheter 30 can be readily passed through the hemostatic valve to the desired position within the patients vascular system. This can be accomplished in various ways. For example, while the plunger subassembly is held in the extended position by the application of thumb pressure on its cap 56, the guidewire 32 can be inserted into the flared mouth 66 in the cap, through the bore 64, through the passageway 54 in the access tube 52, through the flared mouth 68, through the main passageway 28 and the passageway (not shown) in the introducing catheter into the artery. The plunger assembly may then be released, i.e., thumb pressure removed from the plunger cap. This enables the biasing spring 46 to quickly carry the plunger assembly to the retracted position (phantom line position shown in FIG. 1 and solid line position shown in FIG. 1A), thereby removing the access tube from the openings in the valve elements 40 and 42. Since the inner diameter of the opening 84 in the valve element 42 is smaller than the outer diameter of the guidewire the resilient material making up that element 42 which is contiguous with the opening 84 expands into engagement with the periphery of the guidewire 32. Such engagement, while not shown herein, is sufficiently tight to prevent blood from flowing through the interface between the valve element and the guidewire, yet is of relatively low friction so that the guidewire may be moved longitudinally and/or rotated about its axis by the physician. As should be appreciated by those skilled in the art this feature is of considerable importance to the physician to facilitate the placement and use of the guidewire.

Once the guidewire 32 is in place, the plunger subassembly is again actuated, i.e., the plunger cap 56 pressed inward, to move the access tube 52 back through the valve elements 40 and 42. The balloon catheter 30 may be slid down the guidewire 32 through the connector 22 in the same manner as described above. Alternatively, the guidewire and balloon catheter may be introduced through the connector as a unit. This is accomplished by actuating the plunger assembly to move the access tube through the valve elements 40 and 42. The catheter on the guidewire can then be passed through the connector 22.

In any case, once the balloon catheter is at a desired position within the body of the patient, the physician may then release his/her thumb pressure from the plunger cap, whereupon the biasing spring will move the plunger subassembly 48 to the retracted position (phantom line position shown in FIG. 1 and solid line position shown in FIG. 1A). The retraction of the access tube out of the valve element 42 enables the resilient material contiguous with opening 84 to expand into engagement with the periphery of the balloon catheter as shown in FIG. 1A. Such engagement is sufficiently tight to prevent blood from flowing through the interface between the valve element and the balloon catheter, yet is of relatively low friction so that the catheter may be moved longitudinally and/or rotated about its axis by the physician to facilitate its placement and/or use.

In order to prevent the plunger assembly from becoming disconnected from the connector, the outer peripheral edge of the housing portion 36 includes an annular rib 90 which is arranged to abut an annular rim 92 projecting from the inner surface of the annular flange 58 of the plunger 50.

In accordance with a commercial embodiment of this invention the valve element 40 is one such as sold by Vernay Laboratories under Part Number VL601M105. The valve element 42 is custom made and is approximately 0.26 inch (6.61 mm) in diameter and approximately 0.7 inch (1.78 mm) thick, with the inner diameter of the opening 84 being 0.010 inch (0.254 mm), with the length of the opening being 0.20 inch (0.51 mm), and with the conical surface extending at a large angle, e.g., approximately 63.8 degrees, to the central longitudinal axis 62.

It should be pointed out at this juncture that the specific valve assembly 20 shown in the drawings herein is merely exemplary of various types of hemostatic valves which ca be constructed in accordance with the teachings of this invention. Thus, the hemostatic valve of this invention need not make use of either or both of the specific valve elements 40 and 42 described above. Rather, the hemostatic valve of this invention may include any type of valve element(s) so long as it(they) is(are) normally closed but can be readily opened by the extension of the access tube therethrough, and which will close about any elongated instrument after the access tube is retracted to establish hemostasis, yet which will still enable maneuverability of the instrument with respect thereto.

As should be appreciated from the foregoing the hemostatic valve of the subject invention is simple in construction, very easy to use gentle and non-damaging to delicate devices used in vascular and other similar procedures, all the while being very effective to establish complete hemostasis. Moreover, the subject invention is suitable for various types of intrabody procedures, depending upon diameters of the devices to be inserted.

Without further elaboration, the foregoing will so fully illustrate my invention that others may, be applying current or future knowledge, adopt the same for use under various conditions of service.

I claim:

1. A hemostatic valve for use in a device having a housing for enabling the introduction of an elongated member into the body of a living being while precluding blood from flowing thereout, said valve being located within said housing and comprising resilient valve means and plunger means, said housing means comprising a hollow interior portion in which said valve means is located, said valve means comprising at least one valve member, said valve means having a small diameter opening and a slit therein, said plunger means being movable and comprising a cap and a tubular member secured thereto, said tubular member having an outer diameter which is larger than the diameter of said opening in said valve means, said tubular member being arranged to be moved into and out of said opening and said slit in said valve means, said cap having an entrance port, said tubular member having a central passageway in communication with said entrance port, said entrance port and said passageway being arranged to enable said elongated member to be readily extended therethrough for location at a desired position within the body of said being when said tubular member is extended through said opening and said slit in said valve means, whereupon said tubular member may be retracted out of said opening and said slit in said valve means thereafter so that said valve means engages the periphery of said elongated member to preclude blood from flowing out of said hemostatic valve, said slit of said valve means automatically closing when said elongated member is moved out of said opening and out of said slit to preclude blood from flowing out of said hemostatic valve.

2. The hemostatic valve of claim 1 additionally comprising spring biasing means coupled to said plunger means.

3. The hemostatic valve of claim 1 wherein said device comprises a Y-connector.

4. The hemostatic valve of Claim 1 wherein said elongated member includes a central longitudinal axis wherein said opening in said valve means engages said elongated member in an interface, and wherein said interface is of sufficiently low friction to enable said elongated member to be slid or rotated with respect to said central longitudinal axis while still precluding the flow of blood through said interface.

5. The hemostatic valve of claim 1 wherein said at least one valve member comprises a pair of valve members, a first one of said valve members having said opening therein, a second one of said valve members having a normally closed aperture therein, said aperture being openable to enable said tubular member and said elongated member to be passed therethrough.

6. The hemostatic valve of claim 5 wherein said first valve member comprises a disk-like element having a conically shaped recess, with said opening being located at the nadir of said recess.

7. The hemostatic valve of claim 6 wherein said second valve member comprise a duck-bill check valve.

8. The hemostatic valve of claim 1 wherein said plunger means additionally comprises a head portion and a body portion, said body portion extending into the interior of said housing means, said head portion be adapted to be pressed by the thumb of a user while said user holds said housing to cause said tubular member to move from a retracted position within said housing means to an extended position wherein said tubular member extends through said opening in said valve member.

9. The hemostatic valve of claim 8 additionally comprising spring biasing means and retaining means, said retaining means being located within the interior of said housing, said spring biasing means being located within the interior of said housing interposed between said retaining mean and said body portion of said plunger means.

10. The hemostatic valve of claim 9 wherein said biasing means comprises a compression spring.

* * * * *